(12) United States Patent
Lan et al.

(10) Patent No.: US 12,370,134 B2
(45) Date of Patent: *Jul. 29, 2025

(54) PERSONAL CARE FORMULATION

(71) Applicants: Dow Global Technologies LLC, Midland, MI (US); Rohm and Haas Company, Collegeville, PA (US); Dow Silicones Corporation, Midland, MI (US)

(72) Inventors: Tian Lan, Langhorne, PA (US); Fanwen Zeng, Audubon, PA (US); Xiaodong Lu, North Wales, PA (US); Inna Shulman, Langhorne, PA (US); Michaeleen L. Pacholski, Collegeville, PA (US); Isabelle Van Reeth, Incourt Walloon Brabant (BE); Helene Dihang, Taisnières-sur-Hon (FR); Tanvi S. Ratani, Pittsburgh, PA (US); Jason S. Fisk, Freeland, MI (US); Tzu-Chi Kuo, Midland, MI (US); Rachael M. Smith, Douglassville, PA (US)

(73) Assignees: Dow Global Technologies LLC, Midland, MI (US); Rohm and Haas Company, Collegeville, PA (US); Dow Silicones Corporation, Midland, MI (US)

( * ) Notice: Subject to any disclaimer, the term of this patent is extended or adjusted under 35 U.S.C. 154(b) by 54 days.

This patent is subject to a terminal disclaimer.

(21) Appl. No.: 17/768,543

(22) PCT Filed: Nov. 18, 2020

(86) PCT No.: PCT/US2020/060975
§ 371 (c)(1),
(2) Date: Apr. 13, 2022

(87) PCT Pub. No.: WO2021/101943
PCT Pub. Date: May 27, 2021

(65) Prior Publication Data
US 2024/0122840 A1 Apr. 18, 2024

Related U.S. Application Data

(60) Provisional application No. 62/938,460, filed on Nov. 21, 2019.

(51) Int. Cl.
*A61K 8/81* (2006.01)
*A61K 8/19* (2006.01)
*A61K 8/891* (2006.01)
*A61Q 1/02* (2006.01)
*A61Q 17/04* (2006.01)

(52) U.S. Cl.
CPC .............. *A61K 8/8152* (2013.01); *A61K 8/19* (2013.01); *A61K 8/891* (2013.01); *A61Q 1/02* (2013.01); *A61Q 17/04* (2013.01); *A61K 2800/43* (2013.01)

(58) Field of Classification Search
CPC ........ A61K 8/8152; A61K 8/19; A61K 8/891; A61K 2800/43; A61Q 1/02; A61Q 17/04
See application file for complete search history.

(56) References Cited

U.S. PATENT DOCUMENTS

| 4,988,788 A | 1/1991 | Takarada et al. |
|---|---|---|
| 6,060,072 A | 5/2000 | Konik et al. |
| 6,534,590 B1 * | 3/2003 | Aso ...................... C09D 183/10 |
| | | 526/279 |
| 9,486,399 B2 | 11/2016 | Zeng et al. |
| 9,789,049 B2 | 10/2017 | Zhang et al. |
| 10,633,539 B2 | 4/2020 | Phukan et al. |
| 2010/0310489 A1 | 12/2010 | Barba et al. |
| 2015/0231043 A1 | 8/2015 | Sasaki et al. |
| 2017/0260393 A1 | 9/2017 | Phukan et al. |

FOREIGN PATENT DOCUMENTS

| CN | 103347491 | 10/2013 |
|---|---|---|
| EP | 2181700 A1 | 5/2010 |

(Continued)

OTHER PUBLICATIONS

Rodriguez, "Correlation of Silicone Incorporation into Hybrid Acrylic Coatings with the Resulting Hydrophobic and Thermal Properties", Macromolecules, 2008, 41, pp. 8537-8546.
Rodriguez, "Polymerization Strategies to Overcome Limiting Monomer Conversion in Silicone-Acrylic Miniemulsion Polymerization", Polymer, 2008, 48, pp. 691-696.
Search Report from corresponding Chinese Application No. 202080076394.2 dated Jun. 27, 2023.

*Primary Examiner* — Robert A Wax
*Assistant Examiner* — John W Lippert, III
(74) *Attorney, Agent, or Firm* — Thomas S. Deibert

(57) ABSTRACT

Personal care formulation is provided having multistage polymer, comprising: acrylate rich stage comprising: (a) structural units of monomer selected from $C_{1-22}$ alkyl (meth)acrylates and structural units of first carbosiloxane monomer of formula (I); and (b) carbosiloxane rich stage, comprising: structural units of second carbosiloxane monomer of formula (I); wherein a is 0 to 3; wherein d is 0 or 1; wherein $R^1$ is selected from hydrogen, $C_{1-10}$ alkyl group and aryl group; wherein $R^2$ is selected from hydrogen and $C_{1-10}$ alkyl group; wherein $R^8$ is —O—Si$(CH_3)_3$ group; wherein Y is selected from formula (II), (III) and (IV); wherein $R^4$ and $R^6$ are selected from hydrogen and methyl group; wherein $R^3$ and $R^5$ are $C_{1-10}$ alkylene group; wherein $R^7$ is $C_{1-10}$ alkyl group; wherein b is 0 to 4 and wherein c is 0 or 1; and wherein the first and second carbosiloxane monomer of formula (I) are same or different.

10 Claims, No Drawings

(56) References Cited

FOREIGN PATENT DOCUMENTS

| EP | 2915524 A1 | 9/2015 |
|----|------------|--------|
| WO | 2018144541 A1 | 8/2018 |

* cited by examiner

PERSONAL CARE FORMULATION

The present invention relates to a personal care formulation. In particular, the present invention relates to a personal care formulation including a multistage polymer, comprising: an acrylate rich stage comprising: (a) structural units of monoethylenically unsaturated non-ionic, acrylate rich stage monomer selected from $C_{1-22}$ alkyl (meth)acrylates and mixtures thereof and structural units of a first carbosiloxane monomer of formula (I); and (b) a carbosiloxane rich stage, comprising: structural units of a second carbosiloxane monomer of formula (I); wherein a is 0 to 3; wherein d is 0 or 1; wherein $R^1$ is selected from hydrogen, $C_{1-10}$ alkyl group and aryl group; wherein $R^2$ is selected from hydrogen and $C_{1-10}$ alkyl group; wherein $R^8$ is —O—Si(CH$_3$)$_3$ group; wherein Y is selected from formula (II), (III) and (IV); wherein $R^4$ and $R^6$ are selected from hydrogen and methyl group; wherein $R^3$ and $R^5$ are a $C_{1-10}$ alkylene group; wherein $R^7$ is $C_{1-10}$ alkyl group; wherein b is 0 to 4; wherein c is 0 or 1; and wherein the first carbosiloxane monomer of formula (I) and the second carbosiloxane monomer of formula (I) are the same or different.

Consumers increasingly desire color cosmetic formulations that provide long wear properties, such that the formulation might be applied once and last through the work day and beyond without the need for refreshing or touching up. Given today's active lifestyles, it is no simple task to provide such long wear color cosmetic formulations.

An approach to providing such cosmetic formulations is disclosed by Konik et al. in U.S. Pat. No. 6,060,072. In U.S. Pat. No. 6,060,072, Konik et al. disclose water proof or water resistant cosmetic compositions which comprise a styrene-ethylene-propylene copolymer in an amount of 5 to 10%, a combination of a PVP/eicosene copolymer and tricontanyl PVP copolymer in an amount of 0.1 to 50%, a $C_{8-9}$ isoparaffin, a $C_{9-12}$ aliphatic hydrocarbon, or a combination thereof, in an amount of 50 to 85%.

Notwithstanding, there remains a need for new color cosmetic formulations that provide effective wear resistance with color retention.

The present invention provides a personal care formulation, comprising: a multistage polymer, comprising: (a) an acrylate rich stage comprising: 63 to 99.9 wt %, based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof; 0.1 to 25 wt %, based on weight of the acrylate rich stage, of structural units of a first carbosiloxane monomer of formula (I)

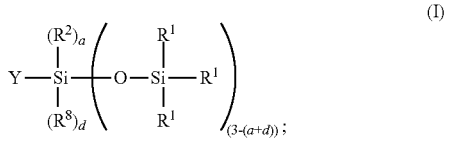

0 to 10 wt %, based on weight of the acrylate rich stage, of structural units of a monoethylenically unsaturated carboxylic acid, acrylate rich stage monomer; and 0 to 2 wt %, based on weight of the acrylate rich stage, of structural units of a multiethylenically unsaturated, acrylate rich stage monomer having at least two ethylenically unsaturated groups per molecule; and (b) a carbosiloxane rich stage, comprising: 0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I)

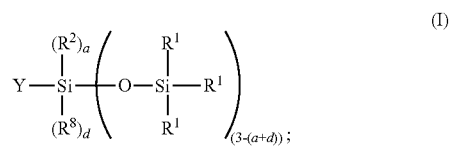

wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si(CH$_3$)$_3$ group; wherein Y is selected from the group consisting of formula (II), (III) and (IV)

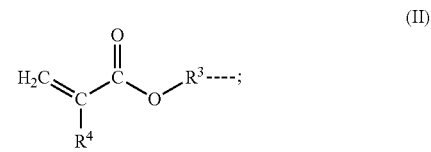

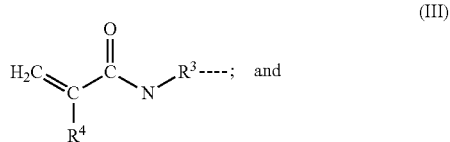

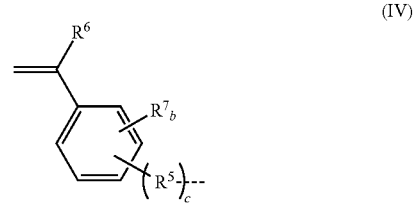

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; wherein the first carbosiloxane monomer of formula (I) and the second carbosiloxane monomer of formula (I) are the same or different.

The present invention provides a method of use, comprising: providing a personal care formulation of the present invention, applying the personal care formulation to the skin of a mammal.

DETAILED DESCRIPTION

We have identified a unique multistage polymer composition having desirable properties for use in personal care formulations, in particular for use in color cosmetic formulations.

Unless otherwise indicated, ratios, percentages, parts, and the like are by weight.

The term "aesthetic characteristics" as used herein and in the appended claims in reference to a personal care formulation refers to visual and tactile sensory properties (e.g., smoothness, tack, lubricity, texture, color, clarity, turbidity, uniformity).

The term "structural units" as used herein and in the appended claims refers to the remnant of the indicated monomer in the claimed polymer; thus a structural unit of n-butyl acrylate is illustrated:

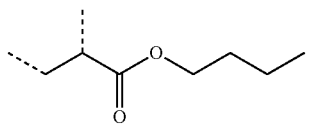

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "cosmetically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the personal care formulation of the present invention, comprises: a multistage polymer (preferably, a multistage emulsion polymer), comprising: (a) (preferably, 60 to 95 wt % (more preferably, 65 to 90 wt %; still more preferably, 70 to 85 wt %; most preferably, 75 to 82 wt %), based on weight of the multistage polymer, of) an acrylate rich stage comprising: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof; 0.1 to 25 wt % (preferably, 1 to <20 wt %; more preferably, 2 to 17.5 wt % most preferably, 4 to 16 wt %), based on weight of the acrylate rich stage, of structural units of a first carbosiloxane monomer of formula (I)

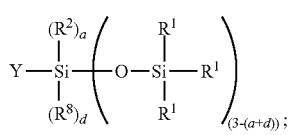

0 to 10 wt % (preferably, 0.5 to 5 wt %; more preferably, 1 to 2 wt %; most preferably, 1.25 to 1.75 wt %), based on weight of the acrylate rich stage, of structural units of a monoethylenically unsaturated carboxylic acid, acrylate rich stage monomer; and 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; and (b) (preferably, 5 to 40 wt %; more preferably, 10 to 35 wt %; still more preferably, 15 to 30 wt %; most preferably, 18 to 25 wt %), based on weight of the multistage polymer, of) a carbosiloxane rich stage, comprising: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I)

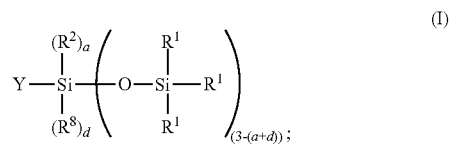

wherein a is 0 to 3 (preferably, 0 to 2; most preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si(CH$_3$)$_3$ group; wherein Y is selected from the group consisting of formula (II), (III) and (IV) (preferably, (II) or (III); most preferably, (II))

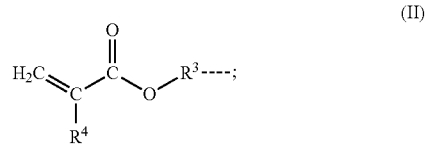

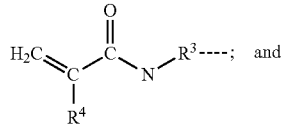

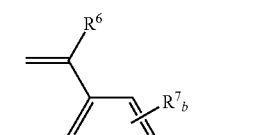

wherein each $R^4$ and $R^6$ are independently selected from the group consisting of a hydrogen and a methyl group (preferably, a methyl group); wherein each $R^3$ and $R^5$ are independently a $C_1$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., —CH$_2$—CH$_2$—CH$_2$—)); wherein each $R^7$ is independently a $C_{1-10}$ alkyl group; wherein b is 0 to 4; wherein c is 0 or 1; and wherein the first carbosiloxane monomer of formula (I) and the second carbosiloxane monomer of formula (I) are the same or different (preferably, wherein the first carbosiloxane monomer of formula (I) and the second carbosiloxane monomer of formula (I) are the same).

Preferably, the personal care formulation of the present invention comprises a multistage polymer (preferably, a multistage emulsion polymer). More preferably, the personal care formulation of the present invention comprises: 0.1 to 10 wt % (preferably, 0.5 to 7.5 wt %; more preferably, 1 to 7 wt %; still more preferably, 3 to 6 wt %; most preferably, 4 to 5 wt %), based on weight of the personal care formulation, of a multistage polymer (preferably, a multistage emulsion polymer). Most preferably, the personal care formulation of the present invention comprises: 0.1 to 10 wt % (preferably, 0.5 to 7.5 wt %; more preferably, 1 to 7 wt %; still more preferably, 3 to 6 wt %; most preferably, 4 to 5 wt %), based on weight of the personal care formulation, of a multistage polymer (preferably, a multistage emulsion polymer); wherein the multistage polymer, comprises an acrylate rich stage and a carbosiloxane rich stage (preferably, an acrylate rich stage as a first stage and a carbosiloxane rich stage as a second stage).

Preferably, the multistage polymer of the present invention comprises an acrylate rich stage. More preferably, the multistage polymer of the present invention, comprises: 60 to 95 wt % (preferably, 65 to 90 wt %; more preferably, 70 to 85 wt %; most preferably, 75 to 82 wt %), based on weight of the multistage polymer, of an acrylate rich stage. Most preferably, the multistage polymer of the present invention, comprises 60 to 95 wt % (preferably, 65 to 90 wt %; more preferably, 70 to 85 wt %; most preferably, 75 to 82 wt %), based on weight of the multistage polymer, of an acrylate rich stage; wherein the acrylate rich stage, comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of $C_{1-22}$ alkyl (meth)acrylates and mixtures thereof; 0.1 to 25 wt % (preferably, 1 to <20 wt %; more preferably, 2 to 17.5 wt % most preferably, 4 to 16 wt %), a first carbosiloxane monomer of formula (I); 0 to 10 wt % (preferably, 0.5 to 5 wt %; more preferably, 1 to 2 wt %; most preferably, 1.25 to 1.75 wt %), based on weight of the acrylate rich stage, of structural units of a monoethylenically unsaturated carboxylic acid, acrylate rich stage monomer; and 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule.

Preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of $C_{1-22}$ alkyl (meth)acrylates and mixtures thereof. More preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of at least two $C_{1-8}$ alkyl (meth)acrylates. Still more preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of at least two $C_{1-4}$ alkyl (meth)acrylates. Yet more preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of at least three $C_{1-4}$ alkyl (meth)acrylates. Most preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of at least three $C_{1-4}$ alkyl (meth)acrylates; wherein the mixture includes butyl acrylate, butyl methacrylate and methyl methacrylate.

Preferably, the acrylate rich stage comprises: 0.1 to 25 wt % (preferably, 1 to <20 wt %; more preferably, 2 to 17.5 wt % most preferably, 4 to 16 wt %), based on weight of the acrylate rich stage, of a first carbosiloxane monomer of formula (I). More preferably, the acrylate rich stage comprises: 0.1 to 25 wt % (preferably, 1 to <20 wt %; more preferably, 2 to 17.5 wt % most preferably, 4 to 16 wt %), based on weight of the acrylate rich stage, of a first carbosiloxane monomer of formula (I), wherein a is 0 to 3 (preferably, 0 to 2; more preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si(CH$_3$)$_3$ group; wherein Y is selected from the group consisting of formula (II), (III) and (IV) (preferably, (II) or (III); more preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., —CH$_2$—CH$_2$—CH$_2$—)); wherein each $R^7$ is independently a $C_{1-10}$ alkyl group; wherein b is 0 to 4 and wherein c is 0 or 1. Most preferably, the carbosiloxane rich stage comprises: 0.1 to 25 wt % (preferably, 1 to <20 wt %; more preferably, 2 to 17.5 wt % most preferably, 4 to 16 wt %), based on weight of the acrylate rich stage, of structural units of a first carbosiloxane monomer of formula (I), wherein a is 1; wherein d is 0; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group.

Preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer. More preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, other derivatives (such as corresponding anhydride, amides and esters) and mixtures thereof. Still more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of acrylic acid, methacrylic acid, itaconic acid, crotonic acid and mixtures thereof. Yet more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of at least one of acrylic acid and methacrylic acid. Most preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is methacrylic acid.

Preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule. More preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof. Still more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of divinylbenzene (DVB), trimethylolpropane diallyl ether, tetra-allyl pentaerythritol, triallyl pentaerythritol, diallyl pentaerythritol, dially phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA), butylene glycol dimethacrylate (BGDMA) and mixtures thereof. Yet more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of DVB, ALMA, EGDMA, HDDA and BGDMA. Yet still more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule includes ALMA. Most preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is ALMA.

Preferably, the multistage polymer of the present invention comprises an carbosiloxane rich stage. More preferably, the multistage polymer of the present invention, comprises: 5 to 40 wt % (preferably, 10 to 35 wt %; more preferably, 15 to 30 wt %; preferably, 18 to 25 wt %), based on weight of the multistage polymer, of a carbosiloxane rich stage. Most preferably, the multistage polymer of the present invention, comprises: 5 to 40 wt % (preferably, 10 to 35 wt %; more preferably, 15 to 30 wt %; preferably, 18 to 25 wt %), based on weight of the multistage polymer, of a carbosiloxane rich stage; wherein the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I).

Preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer. More preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer contains at least one radically polymerizable vinyl group per molecule. Still more preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); monoethylenically unsaturated carboxylic acids (e.g., (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); aromatic vinyl monomers (e.g., styrene, vinyl toluene, benzyl acrylate, benzyl methacrylate, phenoxyethyl acrylate, phenoxyethyl methacrylate, vinyl pyrrolidone); and mixtures thereof. Yet more preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, methacrylic acid and mixtures thereof. Most preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer includes methyl methacrylate and methacrylic acid.

Preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I). More preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I), wherein a is 0 to 3 (preferably, 0 to 2; more preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si(CH$_3$)$_3$ group; wherein Y is selected from the group consisting of formula (II), (III) and (IV) (preferably, (II) or (III); more preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., —CH$_2$—CH$_2$—CH$_2$—)); wherein each $R^7$ is independently a $C_{1-10}$ alkyl group; wherein b is 0 to 4 and wherein c is 0 or 1. Most preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I), wherein a is 1; wherein d is 0; wherein each $R^1$ is a methyl group; wherein $R^2$ is a methyl group; wherein Y is of formula (II); wherein each $R^3$ is a $C_{3-5}$ alkylene group; and wherein each $R^4$ is a methyl group.

Preferably, the personal care formulation of the present invention, further comprises a cosmetically acceptable carrier. More preferably, the personal care formulation of the present invention, comprises: 30 to 92 wt % (preferably, 35 to 92 wt %; more preferably, 40 to 80 wt %) of a cosmetically acceptable carrier. Most preferably, the personal care formulation of the present invention, comprises 30 to 92 wt % (preferably, 35 to 92 wt %; more preferably, 40 to 80 wt %) of a cosmetically acceptable carrier; wherein the multi-stage polymer is dispersed in the cosmetically acceptable carrier.

Preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable carrier is selected to be capable of evaporating upon application of the personal care formulation to mammalian skin (preferably, human skin).

Preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable is selected from the group consisting of water (e.g., deionized, distilled water); emulsions (e.g., oil-in-water emulsion, water-in-oil emulsion); alcohols (e.g., $C_{1-4}$ straight or branched chain alcohols such as ethyl alcohol, propyl alcohol, isopropyl alcohol, butyl alcohol); glycols (e.g., ethylene glycol, propylene glycol, butylene glycol, pentylene glycol, hexylene glycol, dipropylene glycol, ethoxydiglycol); glycerin; butyl cellosolve and mixtures thereof. More preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable carrier includes water (preferably, at least one of deionized water and distilled water; more preferably, deionized, distilled water).

Preferably, the personal care formulation of the present invention, further comprises: a color ingredient. More preferably, the personal care formulation of the present invention, further comprises a color ingredient; wherein the color ingredient is selected from the group consisting of inorganic pigments, organic pigments, aqueous pigment dispersions and mixtures thereof. Still more preferably, the personal care formulation of the present invention, further comprises a color ingredient; wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide and mixtures thereof. Still more preferably, the personal care formulation of the present invention, further comprises a color ingredient; wherein the color ingredient includes at least one iron oxide and titanium dioxide. Most preferably, the personal care formulation of the present invention, further comprises a color ingredient; wherein the color ingredient includes a mixture of iron oxides and titanium dioxide.

Preferably, the personal care formulation of the present invention, further comprises a color ingredient, wherein the color ingredient is a pigment. More preferably, the personal care formulation of the present invention, further comprises a color ingredient, wherein the color ingredient is a pigment and wherein the pigment has a surface treatment (e.g., sodium glycerophosphate, phytic acid (and) sodium hydroxide, PEG-12 dimethicone, dimethicone, hydrogen dimethicone, methicone, lauroyl lysine, hydrogenated lecithin, perfluorooctyl triethoxysilane (and) polyperfluoromethylisopropyl ether, ammonium $C_{6-16}$ perfluoroalkylethyl phosphate). Still more preferably, the personal care formulation of the present invention, further comprises a color ingredient; wherein the color ingredient is a pigment; wherein the pigment has a surface treatment and wherein the surface treatment is formed through treatment of the pigment with a surface treatment agent selected from the group consisting of an alkyl silane, a halogenated phosphonate, a halogenated organosilane or a combination thereof. Most preferably, the personal care formulation of the present invention, further comprises a color ingredient; wherein the color ingredient is a pigment; wherein the pigment has a surface treatment and wherein the surface treatment is formed through treatment of the pigment with a surface treatment agent selected from the group consisting of sodium perfluorohexylethylphosphonate, triethoxy caprylylsilane, perfluorooctyltriethoxysilane and mixtures thereof.

Preferably, the personal care formulation of the present invention, further comprises a suncare active. More preferably, the personal care formulation of the present invention, comprises 0.1 to 70 wt % (preferably, 5 to 65 wt %; more preferably, 7.5 to 60 wt %; most preferably, 10 to 55 wt %) of a suncare active. More preferably, the personal care formulation of the present invention comprises 0.1 to 70 wt % (preferably, 5 to 65 wt %; more preferably, 7.5 to 60 wt %; most preferably, 10 to 55 wt %) of a suncare active; wherein the suncare active is a UV radiation absorbing agent. Still more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent selected from the group consisting of physical blockers (e.g., red petrolatum, titanium dioxide, zinc oxide) and chemical absorbers (e.g., 1-(4-methoxyphenol)-3-(4-tert-butylphenyl) propane-1,3-dione (INCI: Butyl Methoxydibenzoylmethane); 2-hydroxy-4-methoxybenzophenone (INCI: B enzophenone-3); dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate (INCI: octocrylene); 2-ethylhexyl-2-hydroxybenzoate (INCI: Ethylhexyl Salicylate); homomenthyl salicylate; glyceryl aminobenzoate; triethanolamine salicylate; digalloyl trioleate; law sone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate (INCI: Homosalate). Yet more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent comprises a mixture of UV radiation absorbing agents. Yet still more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent is a mixture of UV absorbing agents including at least one of 1-(4-methoxyphenol)-3-(4-tert-butylphenyl)propane-1,3-dione; 2-ethylhexyl-2-hydroxybenzoate; 2-ethyhexyl-2-cyano-3,3-diphenyl-2-propenoate; 2-hydroxy-4-methoxybenzophenone and 3,3,5-trimethylcyclohexyl 2-hydroxybenzoate. Most preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent is a mixture of UV absorbing agents including 1-(4-methoxyphenol)-3-(4-tert-butylphenyl)propane-1,3-dione; 2-ethylhexyl 2-hydroxybenzoate; 2-ethyhexyl-2-cyano-3,3-diphenyl-2-propenoate and 2-hydroxy-4-methoxybenzophenone.

Preferably, the personal care formulation of the present invention, further comprises 0 to 20 wt % (preferably, 0.5 to 15 wt %; more preferably, 1 to 10 wt %; most preferably, 2 to 5 wt %) of a SPF booster. Preferably, the SPF booster is not an active ingredient, but is designed to enhance the effectiveness of the sunscreen actives present in the formulation. Suitable SPF boosters include, but are not limited to, styrene/acrylates copolymer, sodium bentonite, highly purified white sodium bentonite, montmorillonite, hydrogel, nanocrystalline cellulose or any combinations thereof. A particularly preferred styrene/acrylates copolymer for use in the suncare formulation of the present invention is sold under the trade name SunSpheres® by The Dow Chemical Company.

Preferably, the personal care formulation of the present invention, optionally, further comprises an optional additive. More preferably, the color cosmetic formulation of the present invention, further comprises an optional additive, wherein the optional additive is selected from the group consisting of water proofing agents, emollients, preservatives, antioxidants, fragrances, humectants, rheology modifiers, aesthetic modifiers, vitamins, skin protectants, oils, emulsifiers, surfactants, pearlizers, consistency factors, thickeners, super fatting agents, stabilizers, polymers, silicone compounds, fats, waxes, lecithins, phospholipids, fillers, light management powders and particles, and mixtures thereof.

Preferably, the personal care formulation of the present invention has a pH of 4 to 9. More preferably, the personal care formulation of the present invention has a pH of 4.5 to 8.5. Still more preferably, the personal care formulation of the present invention has a pH of 5.0 to 8.0. Most preferably, the personal care formulation of the present invention has a pH of 5.5 to 7.5.

Preferably, the personal care formulation of the present invention is provided a product form selected from the group consisting of a cream, an aqueous solution, an oil, an ointment, a paste, a gel, a lotion, a milk, a foam, a stick and a suspension.

The multistage polymer of the present invention can be prepared by conventional polymerization techniques, such as, for example, by emulsion polymerization. Preferably, the multistage polymer of the present invention is an emulsion polymer. More preferably, the multistage polymer of the present invention is an emulsion polymer, wherein the acrylate rich stage is a first stage of the emulstion polymer and the carboxiloxane rich stage is a second stage of the emulsion polymer.

The personal care formulation of the present invention is useful for at least one of treating (e.g., moisturizing; protecting from harmful effects of exposure to the sun) and enhancing the appearance of skin through application to the skin. Preferably, the personal care formulation of the present invention applies easily to the skin. When provided in the form of a color cosmetic formulation, the personal care formulation of the present invention leaves a clear vivid color that remains in place at least through the work day and preferably thereafter.

Some embodiments of the present invention will now be described in detail in the following Examples.

The monomer abbreviations used in the Examples are described in TABLE 1.

TABLE 1

| Abbreviation | Monomer |
| --- | --- |
| BA | Butyl Acrylate |
| BMA | Butyl Methacrylate |
| MMA | Methyl Methacrylate |

TABLE 1-continued

| Abbreviation | Monomer |
| --- | --- |
| MAA | Methacrylic Acid |
| ALMA | Allyl Methacrylate |
| MD'M-ALMA | 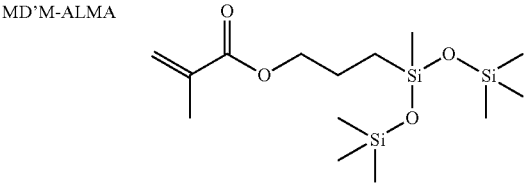 |

Example SC: Multistage Polymer

A 2-liter round-bottom flask (equipped with an overhead stirrer, thermocouple, condenser and inlets for the addition of monomer and initiators) was charged with deionized water (262.0 g), 50% CAVASOL™ W7 MTL (cyclodextrin from Wacker Fine Chemicals) (15.2 g), 31.5% Aerosol™ A102 surfactant (20.5 g) (from Solvay) and sodium carbonate (3.4 g). The flask contents were stirred and heated to 85° C.

An acrylate rich monomer emulsion was prepared by charging deionized water (294.9 g) and 31.5% Aerosol™ A102 surfactant (8.7 g) to a first container and set to stir. Once the surfactant was incorporated into the water the following monomers were added slowly to the first container with continued stirring: BA (182.4 g), BMA (264.5 g), MMA (152.0 g), MAA (9.1 g) and ALMA (0.5 g).

A carbosiloxane rich monomer emulsion was prepared by charging deionized water (76.0 g) and 31.5% Aerosol™ A102 surfactant (2.2 g) to a second container and set to stir. Once the surfactant was incorporated into the water the following monomers were added slowly to the second container with continued stirring: MD'M-ALMA (121.6 g), MMA (28.1 g) and MAA (2.3 g). The carboxiloxane rich monomer emulsion was further emulsified using the homogenization at 7,000 rpm for 10 min.

A cofeed catalyst solution was prepared containing sodium persulfate (1.5 g) and deionized water (40.3 g).

A cofeed buffer solution was prepared containing sodium carbonate (1.5 g) and deionized water (40.3 g).

At a reaction set point temperature of 85° C., 34.2 g of the acrylate rich monomer emulsion from the first container along with a deionized water rinse (15.2 g) was charged to the flask contents. An initiator solution of sodium persulfate (3.4 g) in deionized water (15.2 g) was then added to the flask contents. After the initial polymerization, the remainder of the acrylate rich monomer emulsion in the first container was cofeed to the flask contents at a rate of 6.05 g/min. for 15 minutes and then at 13.01 g/min for 60 minutes. Simultaneously with the acrylate rich monomer emulsion cofeed, the cofeed catalyst solution and the cofeed buffer solution were added to the reactor contents at a rate of 0.44 g/min. for 95 minutes.

Following the addition of the acrylate rich monomer emulsion, the carbosiloxane rich monomer emulsion in the second container was added to the reactor contents at a rate of 11.51 g/min. for 20 minutes. After completion of the various feeds, the contents of the flask were chased to reduce the amount of residual monomers, providing the product multistage polymer.

Examples S1-S4: Multistage Polymer

Multistage polymers were prepared substantially as described in Example SC the appropriate changes being made reflecting the total wt % of the acrylate rich stage and the carbosiloxane rich stage in the respective multistage polymers of Examples S1-S4 with the acrylate rich stage monomers and the carbosiloxane rich stage monomers in the respective stages as noted in TABLE 2.

TABLE 2

| | Multistage polymer | | | | | | | | | |
|---|---|---|---|---|---|---|---|---|---|---|
| | Acrylate rich stage | | | | | | Carbosiloxane rich stage | | | |
| | Monomer (wt %) | | | | | | Monomer (wt %) | | | |
| Ex | Total wt % | BA | BMA | MMA | MAA | MD'M-ALMA | ALMA | Total wt % | MAA | MMA | MD'M-ALMA |
| SC | 80 | 30 | 43.5 | 25 | 1.5 | — | 0.075 | 20 | 1.5 | 18.5 | 80 |
| S1 | 80 | 25 | 43.5 | 25 | 1.5 | 5 | 0.075 | 20 | 1.5 | 18.5 | 80 |
| S2 | 80 | 20 | 43.5 | 25 | 1.5 | 10 | 0.075 | 20 | 1.5 | 18.5 | 80 |
| S3 | 80 | 15 | 43.5 | 25 | 1.5 | 15 | 0.075 | 20 | 1.5 | 18.5 | 80 |
| S4 | 80 | 10 | 43.5 | 25 | 1.5 | 20 | 0.075 | 20 | 1.5 | 18.5 | 80 |

Polymer Properties

The product multistage polymers prepared according to Comparative Example SC and Examples S1-S4 were analyzed for percent solids, pH, mean particle size (using Brookhaven Instruments BI-90 particle size analyzer) and glass transition temperature, $T_g$, as measured using a TA instruments model 2920 Differential Scanning Calorimeter (DSC). The results are provided in TABLE 3.

TABLE 3

| Test Material Example | % solids | pH | PS (nm) | $T_g$ (° C.) |
|---|---|---|---|---|
| SC | 44.4 | 6.5 | 134 | 11 |
| S1 | 44.0 | 5.5 | 132 | 19 |
| S2 | 46.0 | 6.2 | 119 | 13 |
| S3 | 44.1 | 6.1 | 134 | 16 |
| S4 | 44.0 | 6.3 | 158 | 22 |

Neat Polymer Film Mechanical Properties

Film mechanical properties were evaluated by tensile test to determine film tensile strength, toughness and flexibility. The neat polymer film was prepared by casting 20 g of the polymer produced according to each of Comparative Example SC and Examples S1-S4 in a 9.4 cm diameter petri dish. The polymer latex was air dried in an environmental controlled room (72° F., 50% RH) until a dried film formed. The dried film was then peeled off from the petri dish and cut into 3 dog bone pieces with neck part at 0.75 inch long and 0.25 inch wide. The dog bone pieces were then tested in an environmental controlled room (72° F., 50% RH) by using an INSTRON 5565 Tensile Tester with stretch speed at 10 inch/min. The results of the tensile test are provided in TABLE 4.

TABLE 4

| Test Material Example | Mechanical Properties | | |
|---|---|---|---|
| | Tensile stress at break (psi) | Toughness | Tensile strain at break (%) |
| Control* | 110.0 | 440.0 | 726.0 |
| SC | 628.4 | 1484.4 | 409.3 |

TABLE 4-continued

| Test Material Example | Mechanical Properties | | |
|---|---|---|---|
| | Tensile stress at break (psi) | Toughness | Tensile strain at break (%) |
| S1 | 720.0 | 1653.0 | 394.0 |
| S2 | 765.0 | 1727.0 | 312.0 |
| S3 | 867.7 | 2191.4 | 309.1 |
| S4 | 969.4 | 1946.9 | 208.2 |

*EPITEX ™ 66 polymer available from The Dow Chemical Company

Water and Sebum Repellency

Water and sebum repellency of a film are dominated by surface energy. High water and sebum repellency for a prolonged period is desired in a variety of applications, such as, for architectural coatings and for personal care applications (e.g., providing long lasting active deposition and rub-off resistance benefits, especially in color cosmetics, sunscreens and anti-pollution products). The water and sebum repellency can be evaluated by measuring the water contact angle and sebum contact angle from the surface of a film. Specifically, films were prepared from the product multistate polymers prepared according to Comparative Example SC and Examples S1-S4 by drawdown with a 3 mil or 6 mil doctor blade on a black plastic chart (available from LENETA P121-16). The drawn films were air dried in an environmental controlled room (72° F. and 50% RH) for at least 72 hours. The dried films were then placed into a fog box for at least 48 hours to remove any residual surfactants from the film surface. After treatment in the fog box, the films were air dried in an environmental controlled room (72° F. and 50% RH) at least 24 hours before making measurements. Both water and sebum contact angles were measured at approximately 4 seconds and at 250 seconds after water or sebum droplets were deposited on the substrate using a drop shape analyzer (Kruss DSA100). For the sebum contact angle measurement, an artificial sebum solution was prepared having the composition noted in TABLE 5. The results of the water and sebum contact angle measurements are provided in TABLE 6.

TABLE 5

| Ingredient | Weight % |
| --- | --- |
| Glyceryl trioleate[1] | 60 |
| Oleic acid[2] | 20 |
| Squalane[3] | 20 |

[1](65% solution) available from Sigma-Aldrich
[2](90% solution) available from Sigma-Aldrich
[3]available from Sigma-Aldrich

TABLE 6

| Test Material | Contact angle | | | |
| --- | --- | --- | --- | --- |
| | Water | | Sebum | |
| Example | 0 s | 250 s | 0 s | 250 s |
| Control* | 73.1 | 68.7 | 19.4 | 10.4 |
| SC | 97.6 | 94.9 | 50.1 | 37.9 |
| S1 | 93.8 | 90.7 | 47.7 | 46.8 |
| S2 | 94.5 | 89.1 | 53.7 | 53.1 |
| S3 | 96.8 | 93.9 | 52.7 | 38.6 |
| S4 | 95.7 | 93.8 | 51.2 | 34.8 |

*EPITEX ™ 66 polymer available from The Dow Chemical Company

Formulation Example G1: Generic Color Cosmetic Formulation

Color cosmetic formulations were prepared having the generic formulations according to Formulation Example G1 noted in TABLE 7. The Phase A ingredients were added to a beaker and mixed until uniform. The Phase B ingredients were then slowly added to the contents of the beaker with mixing until uniform. The Phase C ingredients were combined in a separate container with mixing until uniform and then slowly added to the contents of the beaker with mixing. The Phase D Test Polymer was then slowly added to the contents of the beaker with mixing until uniform. The Phase E ingredient was then added to the contents of the beaker with mixing until uniform. The Phase F ingredient was then added to the contents of the beaker. The beaker contents were then mixed until uniform to provide the product color cosmetic formulation.

TABLE 7

| Phase | Ingredient INCI name | Parts by weight (pbW) |
| --- | --- | --- |
| A | Isododecane[1] | 10.9 |
| A | Iron Oxide dimethicone[2] | 0.06 |
| A | Iron Oxide (CI 77491), dimethicone[3] | 0.23 |
| A | Iron Oxide (CI 77492), dimethicone[4] | 0.99 |
| A | Titanium Dioxide, dimethicone[5] | 0.85 |
| B | Lauryl PEG-10 Tris(trimethylsiloxy)silyethyl Dimeticone[6] | 5.5 |
| B | Caprylyl Methicone[7] | 3.0 |
| C | Deionized water | 43 |
| C | Sodium chloride | 0.91 |
| C | Glycerin | 4.5 |
| C | Phenoxyethanol (and) Ethylhexylglycerin[8] | 0.91 |

TABLE 7-continued

| Phase | Ingredient INCI name | Parts by weight (pbW) |
| --- | --- | --- |
| D | Test Polymer (on a polymer solids basis) | 4.5 |
| E | Isododecane[1] | 9.1 |
| F | Deionized water | q.s. 100 |

[1]Available from Presperse under the tradename Permethyl ® 99A.
[2]Available from Miyoshi America under tradename SAT-B-335198.
[3]Available from Miyoshi America under tradename SAT-R-338075.
[4]Available from Miyoshi America under tradename SAT-Y-338073.
[5]Available from Miyoshi America under tradename SAT-TRI-77891.
[6]Available from The Dow Chemical Company under the tradename Dowsil ™ ES-5300.
[7]Available from The Dow Chemical Company under the tradename Dowsil ™ FZ-3196.
[8]Available from Schulke Inc. under the tradename euxyl ® PE 9010.

Comparative Examples $C_1$-$C_3$ and Examples 1-4: Color Cosmetic Formulations The color cosmetic formulations of Comparative Examples $C_1$-$C_3$ and Examples 1-4 were prepared according to Formulation Example G1 with varying Test Polymer as noted in TABLE 8.

Wear Resistance

The color cosmetic formulations prepared according to Comparative Examples $C_1$-$C_3$ and Examples 1-4 were each coated on white vinyl charts (available from Leneta) using a doctor blade film applicator with the gap set at 6 mils (0.1524 mm) and allowed to dry at 22° C. for at least 24 hours. The color reading of each sample was then measured using a color spectrophotometer from BYK-Gardner. The wear resistance of the deposited film of color cosmetic formulations was characterized by the change (ΔE) before and after abrasion with a pre-cut bath towel (55 mm×45 mm). The bath towel was fixed to a moving robotic part that moves back and forth periodically at a constant speed. The film was abraded by the bath towel by 3 wear cycles under a pressure of approximately 600 Pa, each wear cycle lasts 6 seconds.

Readings were taken from ten points on each deposited film. The average of the ten readings from each film is provided in TABLE 8.

TABLE 8

| Example | Polymer | ΔE |
| --- | --- | --- |
| Comp. Example C1 | Caprylyl Methicone[1] | 8.9 |
| Comp. Example C2 | Epitex ™ 66 TM | 5.1 |
| Comp. Example C3 | SC | 6.0 |
| Example 1 | S1 | 3.4 |
| Example 2 | S2 | 1.2 |
| Example 3 | S3 | 3.0 |
| Example 4 | S4 | 8.8 |

[1]Available from The Dow Chemical Company under the tradename Dowsil ™ FZ-3196.
[2]Polymer available from The Dow Chemical Company

We claim:

1. A personal care formulation, comprising: a multistage polymer, comprising:
    (a) an acrylate rich stage comprising:
        63 to 99.9 wt %, based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof;

0.1 to 25 wt %, based on weight of the acrylate rich stage, of a first carbosiloxane monomer of formula (I)

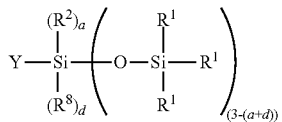

(I)

0 to 10 wt %, based on weight of the acrylate rich stage, of structural units of a monoethylenically unsaturated carboxylic acid, acrylate rich stage monomer; and 0 to 2 wt %, based on weight of the acrylate rich stage, of structural units of a multiethylenically unsaturated, acrylate rich stage monomer having at least two ethylenically unsaturated groups per molecule; and (b) a carbosiloxane rich stage, comprising:

0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I)

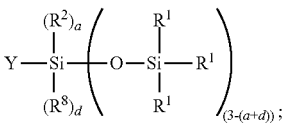

(I)

wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si(CH$_3$)$_3$ group; wherein Y is selected from the group consisting of formula (II), (III) and (IV)

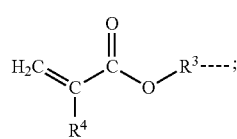

(II)

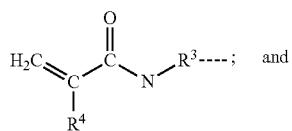

(III)

and

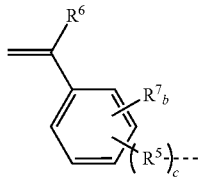

(IV)

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; and wherein the first carbosiloxane monomer of formula (I) and the second carbosiloxane monomer of formula (I) are the same or different.

2. The personal care formulation of claim 1,
wherein the monoethylenically unsaturated non-ionic, acrylate rich stage monomer is selected from the group consisting of a mixture of $C_{1-4}$ alkyl (meth)acrylates;
wherein the monoethylenically unsaturated carboxylic acid, acrylate rich stage monomer is selected from the group consisting of acrylic acid, methacrylic acid, itaconic acid, crotonic acid and mixtures thereof;
wherein the multiethylenically unsaturated, acrylate rich stage monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof;
wherein the vinyl monomer is selected from the group consisting of a mixture of methacrylic acid and methyl methacrylate;
wherein the first carbosiloxane monomer and the second carbosiloxane monomer are the same; and
wherein a is 1; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group.

3. The personal care formulation of claim 2, further comprising a cosmetically acceptable carrier.

4. The personal care formulation of claim 3, wherein the cosmetically acceptable carrier includes water.

5. The personal care formulation of claim 4, further comprising a color ingredient.

6. The personal care formulation of claim 5, wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide and mixtures thereof.

7. The personal care formulation of claim 5, wherein the color ingredient includes at least one iron oxides.

8. The personal care formulation of claim 3, further comprising a suncare active.

9. The personal care formulation of claim 8, wherein the suncare active is a UV radiation absorbing agent is selected from the group consisting of physical blockers and chemical absorbers.

10. The personal care formulation of claim 9, wherein the suncare active is a UV radiation absorbing agent selected from the group consisting of red petrolatum; titanium dioxide; zinc oxide; 1-(4-methoxyphenol)-3-(4-tert-butylphenyl) propane-1,3-dione; 2-hydroxy-4-methoxybenzophenone; dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate; 2-ethylhexyl-2-hydroxybenzoate; homomenthyl salicylate; glyceryl aminobenzoate; triethanolamine salicylate; digalloyl trioleate; lawsone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate and mixtures thereof.

* * * * *